United States Patent [19]

Kiehs et al.

[11] 4,140,725
[45] Feb. 20, 1979

[54] PYROCATECHOL ETHERS

[75] Inventors: Karl Kiehs, Lampertheim; Rolf Huber, Ludwigshafen, both of Fed. Rep. of Germany

[73] Assignee: BASF Aktiengesellschaft, Ludwigshafen, Fed. Rep. of Germany

[21] Appl. No.: 828,290

[22] Filed: Aug. 29, 1977

Related U.S. Application Data

[62] Division of Ser. No. 409,330, Oct. 24, 1973, abandoned.

[30] Foreign Application Priority Data

Oct. 25, 1972 [DE] Fed. Rep. of Germany ....... 2252198

[51] Int. Cl.² ............................................. C07C 43/22
[52] U.S. Cl. ............................ 568/593; 260/345.9 R; 560/132; 560/133; 424/300; 560/254
[58] Field of Search ..................................... 260/613 D

[56] References Cited

U.S. PATENT DOCUMENTS 2,508,917 5/1950 Harris et al. ................. 260/613 D X
2,528,139 10/1950 Harris et al. ................. 260/613 D X

OTHER PUBLICATIONS

Kiehs et al., Chem. Abs., vol. 81, (1974), 25428f, 25352b.

Primary Examiner—Bernard Helfin
Attorney, Agent, or Firm—Keil & Witherspoon

[57] ABSTRACT

Compounds of the formula:

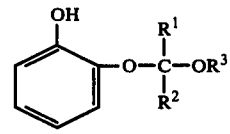

are disclosed which compound are used to prepare carbamates which are stated to have utility as plant protecting agents and insecticides.

6 Claims, No Drawings

PYROCATECHOL ETHERS

This is a division, of application Ser. No. 409,330 filed Oct. 24, 1973, now abandoned.

The present invention relates to new and valuable pyrocatechol ethers and processes for their production.

German Pat. No. 566,033 discloses that alcoholic or phenolic hydroxyl groups are capable of reacting with vinyl or α-haloethers with the formation of acetals which are stable to alkali (cf. also Houben-Weyl, "Methoden der organischen Chemie," volume 6/3, pages 186 and 229).

It is also known (for example from B.J. Chem. Soc., 1927, 1664; U.S. Pat. No. 3,202,573) that in an attempt to carry out a partial alkylation of only one hydroxyl group of pyrocatechol this latter and the alkylating agent are lost in considerable quantities due to the formation, as byproduct, of the nonexploitable diether.

We have found that the valuable new ethers or pyrocatechol having the formula (I):

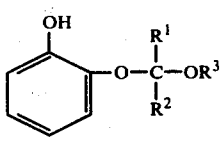

in which $R^1$ is hydrogen or lower alkyl ($C_1$ to $C_4$);

$R^2$ is unsubstituted or substituted (by halogen (Cl, Br, I), methoxy or ethoxy) lower alkyl ($C_1$ to $C_3$) or benzyl;

$R^3$ is alkyl ($C_1$ to $C_4$), cycloalkyl ($C_3$ to $C_7$), β-chloroethyl, alkoxyalkyl (methoxyethyl, ethoxyethyl), alkenyl (up to $C_4$), alkynyl (up to $C_4$), acyl (acetyl); and moreover $R^1$ and $R^2$ together with the carbon atom whose substituents they are and also $R^1$ and $R^3$ together with the carbon or oxygen atom whose substituents they are, form a five-membered or six-membered ring (cyclopentyl, cyclohexyl, tetrahydrofuranyl, tetrahydropyranyl) are obtained in a simple manner and excellent yields when pyrocatechol is reacted with preferably the amount required for etherification of one hydroxyl group of pyrocatechol, or up to about a 50% excess or deficiency of this amount, of a vinyl ether of the formula:

$$R-OR^3,$$

where R is vinyl or vinyl bearing lower alkyl (up to $C_3$) as a substituent and $R^3$ has the above meanings, with or without the addition of a catalytically-acting substance such as an acid-reacting substance, e.g. a mineral acid, acid salt, organic acid, α-haloether, organic or inorganic acid chloride, an ion exchanger or a Lewis acid, for example $AlCl_3$, $FeCl_3$, $BF_3$ and the like, in a temperature range of from $-5°$ C. to $120°$ C. and preferably at $40°$ C. to $50°$ C. and/or with the addition of a solvent or diluent which is inert to the reactants, for example an ether (diethyl ether, tetrahydrofuran, dioxane), a hydrocarbon (for example n-hexane, benzene, toluene or xylene), halohydrocarbon ($CH_2Cl_2$, $CHCl_3$ or $CCl_4$).

The new compounds are important intermediates for the production of active ingredients for plant protection agents and pharmaceutical and veterinary products.

If pyrocatechol is reacted with vinyl methyl ether, the reaction may be illustrated by the following equation:

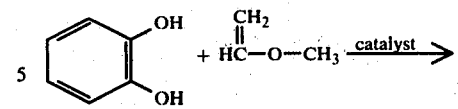

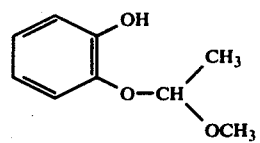

The abovementioned compounds are preferably used as catalysts.

The products according to the invention may also be prepared by reaction of preferably equimolar amounts or an excess or deficiency of up to about 50% of an α-haloester of the formula:

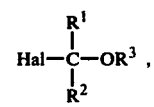

where Hal is Cl, Br or I and the radicals $R^1$, $R^2$ and $R^3$ have the above meanings, with a salt of pyrocatechol or with pyrocatechol in the presence of an organic or inorganic base (for example an alcoholate, alkali metal hydroxide, alkaline earth metal hydroxide or suitable amine) or a substance having an alkaline reaction, such as an alkali or alkaline earth metal carbonate.

The following equation illustrates the reaction:

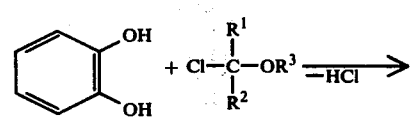

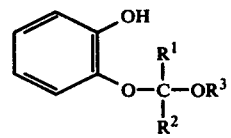

The radicals $R^1$, $R^2$ and $R^3$ have the above meanings. It is preferred to dilute the reactants with a solvent, for example from 5 to 80% by weight of an ether (diethyl ether, tetrahydrofuran) or an aromatic hydrocarbon (benzene, toluene, xylene).

The vinyl ethers and α-haloethers used for the reaction are known from the literature and are also readily prepared industrially (cf. for example W. Reppe et al., Ann., 601, (1956), 98.

Depending on the excess of vinyl ether or α-haloether used in the abovementioned processes there are formed corresponding amounts of new bisethers of the formula (II):

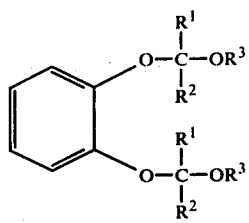

(II).

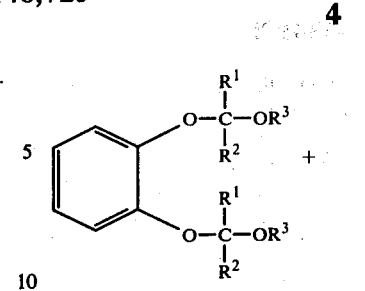

The radicals $R^1$, $R^2$ and $R^3$ have the above meanings.

The abovementioned bisethers may be prepared in quantitative yields preferably by reaction of pyrocatechol with at least twice the molar amount of a vinyl ether.

The catalysts and reaction conditions as regards temperature and solvents are analogous to those given for the production of compounds of formula (I).

Another process for the production of compounds of the formula (I) consists in reacting a bisether of the formula (II) with pyrocatechol according to the following equation:

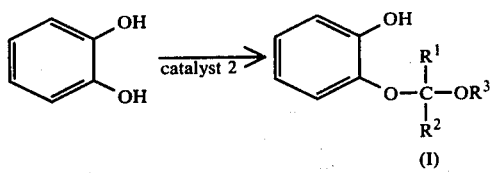

The radicals $R^1$, $R^2$ and $R^3$, the catalysts and the reaction conditions are the same as in the production of compounds of the formula (I) from vinyl ethers.

The new pyrocatechol derivatives of the formulae (I) and (II) are obtained in the form of colorless oils which after stabilization with organic or inorganic bases can be distilled in vacuo without decomposition. Compounds which may be prepared by the process of the invention are listed below:

| $R^1$ | $R^2$ | $R^3$ | bp ° C.; $n_D^{25}$ |
|---|---|---|---|
| H | H | CH₃ | bp(0.4 mm): 89 to 93 |
| H | H | C₂H₅ | bp(0.1 mm): 90 to 100 |
| H | CH₃ | CH₃ | bp(0.5 mm): 85 to 90 |
| H | CH₃ | C₂H₅ | bp(1 mm): 78 to 81 |
| H | CH₃ | n-C₃H₇ | bp(1 mm): 96 to 98 |
| H | CH₃ | i-C₃H₇ | bp(1 mm): 89 to 94 |
| H | CH₃ | i-C₄H₉ | bp(0.2 mm): 94 to 98 |
| H | CH₃ | —cyclohexyl | bp(0.2 mm): 128 to 135 |
| H | CH₃ | —phenyl | bp(4 mm): 132 to 136 |
| H | CH₃ | COCH₃ | $n_D^{25}$: 1.5075 |
| H | CH₃ | COC₂H₅ | $n_D^{25}$: 1.4905 |
| H | CH₃ | —CH₂—CH=CH₂ | |
| H | CH₃ | —CH₂—C≡CH | |
| H | CH₃ | —CH(CH₃)—C≡CH | |
| H | CH₃ | —CH₂—CH₂—OCH₂H₅ | $n_D^{25}$: 1.5135 |
| H | CH₃ | —CH₂—CH₂—OC₂H₅ | $n_D^{25}$: 1.5146 |
| H | CH₂Cl | —CH₃ | $n_D^{25}$: 1.4975 |
| H | CH₂Cl | —C₂H₅ | $n_D^{25}$: 1.5012 |
| H | CH₂Cl | —CH₂—CH₂Cl | $n_D^{25}$: 1.5340 |
| H | CH₂Cl | COCH₃ | |
| H | CH₂Br | CH₃ | |
| H | CH₂I | CH₃ | bp(1.5 mm): 105 to 113 |
| H | C₂H₅ | CH₃ | bp(0.5 mm): 100 to 103 |
| H | C₂H₅ | C₂H₅ | $n_D^{25}$: 1.5023 |
| H | C₂H₅ | CH₂—C≡CH | |
| H | CH₂—CH₂Cl | CH₃ | |
| H | CH₂—CHCl-CH₃ | CH₃ | |
| H | CH₂—CHBr-CH₃ | CH₃ | |
| H | CH₂—CHCl-C₂H₅ | CH₃ | |
| H | n-C₃H₇ | CH₃ | |
| H | i-C₃H₇ | CH₃ | |

-continued

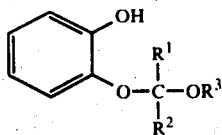

| R¹ | R² | R³ | bp °C.; $n_D^{25}$ |
|---|---|---|---|
| H | CH=CH₂ | CH₃ | |
| H | C≡CH | CH₃ | |
| H | CH₂—C≡CH | CH₃ | |
| H | CH₂—C₆H₅ | CH₃ | |
| CH₃ | CH₃ | CH₃ | bp$_{(0.3\ mm)}$: 95 to 100 |
| CH₃ | CH₃ | C₂H₅ | |
| CH₃ | CH₂Cl | CH₃ | $n_D^{25}$: 1.5024 |
| CH₃ | CH₂Cl | C₂H₅ | |
| CH₃ | CH₂Br | CH₃ | |
| CH₃ | CH₂Br | C₂H₅ | |
| CH₃ | C₂H₅ | CH₃ | |
| CH₃ | n-C₃H₇ | CH₃ | |
| CH₃ | i-C₃H₇ | CH₃ | |
| C₂H₅ | C₂H₅ | CH₃ | |
| cyclopentyl | | CH₃ | |
| cyclohexyl | | CH₃ | | bp$_{(0.5\ mm)}$: 115 to 118

Formula (II)

| R¹ | R² | R³ | bp |
|---|---|---|---|
| H | H | CH₃ | bp$_{(0.4\ mm)}$: 105 to 109 |
| H | CH₃ | CH₃ | bp$_{0.5\ mm)}$: 99 to 105 |
| H | CH₃ | C₂H₅ | bp$_{(0.3\ mm)}$: 97 to 102 |
| H | CH₃ | i-C₄H₉ | bp$_{(0.3\ mm)}$: 124 to 128 |

The new compounds are of great importance as precursors for plant protection agents and pharmaceutical products.

For example by reaction of compounds of formula (I) with methyl isocyanate, active substances may be prepared which have a good insecticidal action both on biting and sucking insects and outstanding effectiveness against red spiders and ticks. At the same time they have only slight phytotoxicity. The action is rapid and prolonged. For this reason the active substances may be used successfully in plant protection for controlling injurious sucking and biting insects and Diptera and for combatting mites (Acarina) both in this and the veterinary field. In this context emphasis may be placed on the excellent effectiveness of the active substances against strains of red spiders which are resistant to phosphoric esters.

The following examples illustrate the invention.

EXAMPLE 1 o-(1-methoxy)-ethoxyphenyl-N-methyl carbamate 34 parts by weight of o-(1-methoxy)-ethoxyphenol is dissolved in 100 parts by weight of toluene. 12 parts by weight of methyl isocyanate is poured in all at once. 2 drops of triethylamine are added and the whole is left to stand overnight. The whole is then concentrated and to the oily residue there is added 100 parts by weight of a mixture of equal parts of toluene and ligroin. 33 parts by weight of colorless crystals are precipitated upon cooling. After recrystallization these crystals melt at 97° to 99° C.

EXAMPLE 2 o-(1-ethoxy)-ethoxyphenyl-N-methyl carbamate 33.4 parts by weight of pyrocatecholmono-N-methyl carbamate is suspended in 100 parts by weight of toluene. 3 drops of concentrated hydrochloric acid are added and then 15 parts by weight of vinyl ethyl ether is dripped in over a period of 10 minutes. The whole is stirred for 1 hour at 80° C. After cooling the product is washed with 50 parts by weight of 3% sodium bicarbonate solution and dried over sodium sulfate, and the solvent is removed. A colorless oil remains which is taken up in 100 parts by weight of a mixture of equal parts of toluene and ligroin. 31 parts by weight of carbamate crystallizes out in the deep freezer. After recrystallization the melting point is 62° to 63° C.

The substances set out in the following Table may be obtained in a similar manner:

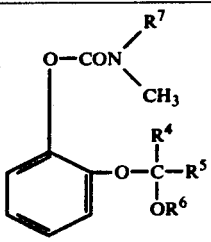

| R[7] | R[4] | R[5] | R[6] | mp. ° C. |
|---|---|---|---|---|
| H | CH$_3$ | H | i-C$_3$H$_7$ | 40 to 45 |
| H | C$_2$H$_5$ | H | CH$_3$ | 88 to 90 |
| H | C$_2$H$_5$ | H | C$_2$H$_5$ | 52 to 54 |
| H | C$_3$H$_7$ | H | CH$_3$ | |
| H | C$_3$H$_7$ | H | C$_2$H$_5$ | |
| H | n-C$_4$H$_9$ | H | CH$_3$ | |
| H | n-C$_4$H$_9$ | H | C$_2$H$_5$ | |
| H | i-C$_4$H$_9$ | H | CH$_3$ | |
| H | n-C$_4$H$_{11}$ | H | CH$_3$ | |
| H | CH$_3$ | CH$_3$ | CH$_3$ | 80 to 82 |
| H | CH$_3$ | CH$_3$ | C$_2$H$_5$ | |
| H | C$_2$H$_5$ | CH$_3$ | CH$_3$ | |
| CH$_3$ | CH$_3$ | H | CH$_3$ | |

Other new active substances are as follows:

| R[7] | R[4] | R[5] | R[6] | mp. ° C. (n$_D^{26}$) |
|---|---|---|---|---|
| H | H | CH$_2$Cl | C$_2$H$_5$ | (1.5125) |
| H | H | CH$_2$Cl | COCH$_3$ | (1.5119) |
| CH$_3$ | H | CH$_2$Cl | C$_2$H$_5$ | (1.5205) |
| CH$_3$ | H | CH$_2$Br | CH$_3$ | (1.5310) |
| H | H | CH$_2$Br | CH$_3$ | 70 to 72 |
| H | H | CH$_2$I | CH$_3$ | (1.5465) |
| CH$_3$ | H | CH$_2$I | CH$_3$ | |
| H | H | CH$_2$—CH$_2$Cl | CH$_3$ | 65 to 66 |
| CH$_3$ | H | CH$_2$—CH$_2$Cl | CH$_3$ | |
| H | H | CHCl—CH$_3$ | CH$_3$ | |
| H | H | CHBrCH$_3$ | CH$_3$O | |
| H | H | CH$_2$—CH$_2$Br | CH$_3$ | |
| H | H | CH$_2$OCH$_3$ | CH$_3$ | |
| CH$_3$ | H | CH$_2$—OCH$_3$ | CH$_3$ | |
| H | H | CH$_2$—CH$_2$—OCH$_3$ | CH$_3$ | (1.5184) |
| H | H | CH(OCH$_3$)—CH$_3$ | CH$_3$ | |
| H | H | COCH$_3$ | CH$_3$ | |
| H | CH$_3$ | CH$_2$Cl | CH$_3$ | 106 to 108 |
| CH$_3$ | CH$_3$ | CH$_2$Cl | CH$_3$ | |
| H | CH$_3$ | CH$_2$Br | CH$_3$ | |
| CH$_3$ | CH$_3$ | CH$_2$Br | CH$_3$ | |
| H | H | CH$_2$—SCH$_3$ | CH$_3$ | |

EXAMPLE 3

(a) o-(1-methoxyethoxy)-phenol 110 parts by weight of pyrocatechol is suspended in 100 parts by weight of toluene. At +5° C. 64 parts by weight of vinyl methyl ether which has a temperature of −40° C. is poured in all at once and then 1 drop of concentrated hydrochloric acid is added. The whole is heated to about +20° C. while stirring, whereupon the reaction commences and the temperature of the contents of the flask rises to about 65° C. External cooling with ice-water may be applied if necessary. The whole is kept for half an hour at 65° C. and then 5 parts by weight of 2-normal caustic soda solution is added. The whole is cooled, and dried by means of sodium sulfate, and the solvent is evaporated in a rotary evaporator. The product is distilled in vacuo. The yield is 155 parts by weight. The boiling point is 85° to 90° C. at 0.5 mm.

Analysis: C$_9$H$_{12}$O$_3$ (168) Calculated: C,64.1; H,7.2. Found: C,64.4; H,7.0.

(b) pyrocatechol-bis-[(1-methoxy)-ethyl]-ether

The reaction described under (a) is repeated but with twice the amount (128 parts by weight) of vinyl methyl ether. 122 parts by weight of a colorless oil is obtained having a boiling point of 99° to 105° C. at 0.5 mm.

Analysis: C$_{12}$H$_{18}$O$_4$ (226) Calculated: C,63.7; H,8.0. Found: C,63.3; H,8.1.

(c) o-(1-methoxyethoxy)-phenol 0.5 parts of SOCl$_2$ is added to 113 parts by weight of pyrocatechol-bis-[(1-methoxy)-ethyl]-ether and 55 parts by weight of pyrocatechol at 40° C. and the whole is stirred at this temperature for half an hour. It is then allowed to cool and 2 parts by volume of 25% by weight aqueous caustic soda solution is added. The product is separated and dried over sodium sulfate and the solvent is evaporated. There remains 168 parts of the abovementioned compound having a boiling point of 85° to 90° C. at 0.5 mm.

EXAMPLE 4

(a) o-(1-ethoxyethoxy)-phenol 220 parts by weight of pyrocatechol is suspended in 200 parts by weight of toluene. After 2 drops of concentrated hydrochloric acid have been added 150 parts by weight of ethyl vinyl ether is dripped in while stirring. The internal temperature is prevented from rising above 65° C. by external cooling with ice. All of the pyrocatechol has dissolved upon completion of the reaction. 5 parts by weight of 2-normal caustic soda solution is added, the whole is allowed to cool, and dried over sodium sulfate, the solvent is removed and the product is distilled in vacuo. The yield is almost quantitative; boiling point 78° to 81° C. at 1 mm; n$_D^{25}$ = 1.5032

Analysis: C$_{10}$H$_{14}$O$_3$ (182). Calculated: C,66.0; H,7.7. Found: C,66.3; H,7.9.

(b) Pyrocatechol-bis-[(1-ethoxy)-ethyl]-ether

The method of (a) is employed, except that 300 parts by weight of ethyl vinyl ether is used instead of 150 parts by weight. 248 parts by weight of a colorless oil is obtained having a boiling point of 97° to 102° C. at 0.3 mm.

Analysis: C$_{14}$H$_{22}$O$_4$ (254) Calculated: C,66.2; H,8.6. Found: C,66.4; H,8.7.

(c) o-(1-ethoxyethoxy)-phenol 127 parts by weight of pyrocatechol-[(1-ethoxy)-ethyl]-ether and 55 parts by weight of pyrocatechol are reacted and processed as described in Example 3(c). The yield is 179 parts of the phenol compound. The boiling point is 79° to 80° C. at 1 mm.

EXAMPLE 5 o-(methoxymethoxy)-phenol 110 parts by weight of pyrocatechol is dissolved in 400 parts by weight of benzene. 101 parts by weight of triethylamine and 81 parts by weight of chloromethyl methyl ether are dripped in simultaneously at ambient temperature in such a manner that the reaction medium has a weakly basic reaction. The whole is then heated for another hour under reflux; it is allowed to cool and the hydrochloride is suction filtered, washed with water, dried over sodium sulfate, concentrated and distilled in vacuo. The yield is 120 parts by weight and the boiling point is 89° C. at 0.4 mm; $n_D^{25} = 1.5150$.

Analysis: $C_8H_{10}O_3$ (154) Calculated: C,62.3; H,6.5. Found: C,62.0; H,6.5.

We claim:

1. A pyrocatechol ether of the formula:

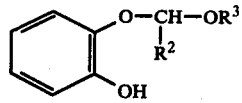

wherein $R^2$ is a monohalo-substituted lower alkyl group with a maximum of 4 carbon atoms, the halo substituent being selected from the group consisting of Cl, Br and I, and $R^3$ is alkyl with a maximum of four carbon atoms.

2. An ether as claimed in claim 1 wherein $R^2$ represents chloromethyl and $R^3$ represents methyl.

3. An ether as claimed in claim 1 wherein $R^2$ represents chloromethyl and $R^3$ represents ethyl.

4. An ether as claimed in claim 1 wherein $R^2$ represents bromomethyl and $R^3$ represents methyl.

5. An ether as claimed in claim 1 wherein $R^2$ represents iodomethyl and $R^3$ represents methyl.

6. An ether as claimed in claim 1 wherein $R^2$ represents —$CH_2$—$CH_2Cl$ and $R^3$ represents methyl.

* * * * *